US008172084B2

(12) United States Patent
Goodrich et al.

(10) Patent No.: US 8,172,084 B2
(45) Date of Patent: May 8, 2012

(54) ABSORBENT ARTICLE PACKAGING

(75) Inventors: Kellie M. Goodrich, Appleton, WI (US);
James A. Boldra, Menasha, WI (US);
Jane L. Clough, Neenah, WI (US);
Edward J. Foley, Greenville, WI (US);
Keith R. Haen, Neenah, WI (US);
Linda K. Lemerande, Waupaca, WI (US); Thomas W. Odorzynski, Green Bay, WI (US); Robert E. Vogt, Neenah, WI (US)

(73) Assignee: Kimberly-Clark Worldwide, Inc., Neenah, WA (US)

( * ) Notice: Subject to any disclaimer, the term of this patent is extended or adjusted under 35 U.S.C. 154(b) by 2151 days.

(21) Appl. No.: 11/027,066

(22) Filed: Dec. 30, 2004

(65) Prior Publication Data
US 2006/0144736 A1 Jul. 6, 2006

(51) Int. Cl.
B65D 75/52 (2006.01)
B65D 75/04 (2006.01)

(52) U.S. Cl. ............... 206/440; 206/494; 604/385.02

(58) Field of Classification Search ............... 206/440, 206/339, 210, 441, 570, 581, 438, 457, 494; 604/385.02
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,041,203 A | 8/1977 | Brock et al. | |
| 4,242,854 A | 1/1981 | Nissen | |
| 4,340,563 A | 7/1982 | Appel et al. | |
| 4,766,029 A | 8/1988 | Brock et al. | |
| 4,934,535 A | 6/1990 | Muckenfuhs et al. | |
| 4,966,286 A | 10/1990 | Muckenfuhs | |
| 5,050,742 A | 9/1991 | Muckenfuhs | |
| 5,054,619 A | 10/1991 | Muckenfuhs | |
| 5,169,706 A | 12/1992 | Collier, IV et al. | |
| 5,382,400 A | 1/1995 | Pike et al. | |
| 5,464,688 A | 11/1995 | Timmons et al. | |
| 5,476,443 A * | 12/1995 | Cartmell et al. | ............... 602/58 |
| 5,540,500 A | 7/1996 | Tanaka | |
| 6,225,522 B1 * | 5/2001 | Schroeder | ............... 602/57 |
| 6,548,432 B1 | 4/2003 | Hisada et al. | |
| 6,802,833 B2 * | 10/2004 | Kudo | ............... 604/385.02 |
| 6,923,320 B2 * | 8/2005 | Grossman | ............... 206/440 |
| 6,923,321 B2 * | 8/2005 | Samolinski et al. | ............... 206/440 |
| 2002/0025752 A1 | 2/2002 | Taniguchi | |
| 2002/0153271 A1 * | 10/2002 | McManus et al. | ............... 206/440 |
| 2003/0120241 A1 | 6/2003 | Sorebo et al. | |
| 2003/0130642 A1 | 7/2003 | Kashiwagi et al. | |
| 2004/0004014 A1 * | 1/2004 | Grossman | ............... 206/440 |
| 2004/0122399 A1 | 6/2004 | McDaniel | |

FOREIGN PATENT DOCUMENTS

| | | |
|---|---|---|
| EP | 0 959 165 A1 | 11/1999 |
| EP | 0 989 222 A1 | 3/2000 |
| EP | 1 300 125 A2 | 4/2003 |
| EP | 1 332 746 A2 | 8/2003 |
| WO | WO 02/058524 A2 | 8/2002 |

OTHER PUBLICATIONS

Exhibit A—Photograph of cardboard packaging for a diaper product manufactured by The Procter & Gamble Company and marketed in the United States under the tradename of Luvs prior to the filing date of the present application.
Exhibit B—Photograph of cardboard packaging for a diaper product manufactured by The Procter & Gamble Company and marketed in the United States under the tradename of Luvs prior to the filing date of the present application.
Exhibit C—Photograph of cardboard packaging for a diaper product manufactured by The Procter & Gamble Company and marketed in the United States under the tradename of Luvs prior to the filing date of the present application.
Exhibit D—Photograph of a diaper product manufactured by The Procter & Gamble Company and marketed in the United States under the tradename of Luvs prior to the filing date of the present application.

* cited by examiner

Primary Examiner — Steven A. Reynolds
(74) Attorney, Agent, or Firm — David J. Arteman; Randall W. Fieldhack

(57) ABSTRACT

A package containing an article. The article includes a first article texture and a second article texture. The package includes a plastic packaging material having an outer surface. Further the first article texture and the second article texture are non-similar and at least a portion of the outer surface has a packaging texture that is a simulant of the first article texture and at least a portion of the outer surface has a packaging texture that is a simulant of the second article texture.

18 Claims, No Drawings

ABSORBENT ARTICLE PACKAGING

BACKGROUND

This disclosure relates to packages and packaging materials for absorbent articles.

Poly-film bags have been used for compressed packaging of absorbent articles. The poly-film bags are made of layers of a thin sheet or film of thermoplastic material, such as polyethylene, which is folded around the absorbent article and then sealed to form a package. These poly-film packages tend to have a glossy exterior with a smooth, plastic look and feel. A disadvantage of the poly-film packaging is that it makes noise when moved. For example, when a diaper is removed from a poly-film package, the package moves and can make sufficient noise to wake a child from a sleepy state. Once the packaging is opened, consumers generally remove all of the articles from the packaging and dispose of the packaging. This can leave the articles loose, difficult to handle, and difficult to store neatly, efficiently, discretely, and without contaminating the articles. Also, due to the packaging, differentiation between various absorbent articles is also difficult for the consumer, particularly without first purchasing the product and removing it from the packaging.

Accordingly, there remains a need for a packaging material and a packaging for products, and particularly absorbent articles.

BRIEF SUMMARY

The present inventors undertook intensive research and development efforts concerning article packaging. While conducting their research, the present inventors discovered unique article packaging. A first version of the present invention involves a package containing an article. The article includes a first article texture and a second article texture. The package includes a plastic packaging material having an outer surface. Further the first article texture and the second article texture are non-similar and at least a portion of the outer surface has a packaging texture that is a simulant of the first article texture and at least a portion of the outer surface has a packaging texture that is a simulant of the second article texture.

Another version of the present invention relates to a packaged absorbent article including packaging, the packaging including a plastic packaging material having an outer surface including a nonwoven material. The packaged absorbent article further including an absorbent article disposed in the packaging. The absorbent article including a liquid permeable bodyside liner, an outer cover, and an absorbent body positioned between the bodyside liner and the outer cover. Further, the outer cover has an article texture and at least a portion of the outer surface has a packaging texture that is a simulant of the article texture. The packaging material has a Qmax of less than or equal to about 0.100 W/m2.

A third version of the present invention relates to a method for packaging articles including heat sealing a plastic packaging material to form a package. The method further including disposing the articles in the package. Further the articles have a first article texture and a second article texture. The first article texture and the second article texture are non-similar. The plastic packaging material has an outer surface, and at least a portion of the outer surface has a packaging texture that is a simulant of the first article texture and at least a portion of the outer surface has a packaging texture that is a simulant of the second article texture.

It is to be understood that both the foregoing general description and the following detailed description are exemplary and are intended to provide further explanation of the invention claimed.

DETAILED DESCRIPTION

Disclosed herein are packaging materials, e.g., for compressed packaging of articles. All ranges disclosed herein are inclusive and combinable (e.g., ranges of "up to about 25 wt %, or, more specifically about 5 wt % to about 20 wt % ," is inclusive of the endpoints and all intermediate values of the ranges of "about 5 wt % to about 25 wt %," etc.). The terms "first," "second," and so forth, herein do not denote any order, quantity, or importance, but rather are used to distinguish one element from another, and the terms "a" and "an" herein do not denote a limitation of quantity, but rather denote the presence of at least one of the referenced item.

The absorbent article packaging can be a simulant of the article; e.g., comprises a look and feel commensurate with the look and feel of the article disposed within the packaging. For example, the packaging can comprise a similar look and/or texture as the product contained in the packaging; e.g., as an outer cover of an absorbent article (such as a diaper, disposable underwear, sanitary garment, and so forth) disposed within the packaging. Hence, the packaging can give a consumer a sense of the product and its quality. Additionally, the packaging material can be quieter (e.g., than a poly-film packaging) such that when product is removed from the packaging, the noise level caused by the product removal is low (e.g., so as not to disturb a sleeping, quiet, calm, and/or groggy baby).

The packaging can optionally be an internal packaging of groups of product (e.g., a group of 5 or so absorbent articles). In this case, a plurality of the internal packaging groups can be disposed in an outer covering (e.g., a plastic covering), wherein the outer covering can be transparent and/or have a transparent portion, such as a window, which shows the internal packaging. The plastic covering, which could be a poly-film container, could also have an opening that enables contact with the inner packaging to enable the consumer to experience the feel of the internal packaging and hence the product, thereby illustrating the quality and differentiating the packaging from similar product's packaging. All or a portion of the outer packaging, as with the internal packaging groups, could be a simulant of the product.

For example, the product can be an article in a folded configuration that defines a two dimensional article with article visual elements (e.g., where the visual elements comprise the article first texture and an article design). The packaging can have a surface that defines package visual elements, such that the package visual elements are a simulant of the article visual elements. The article visual elements comprise the texture as well as design(s). The designs can comprise, for example, waist band(s), leg cuff(s), attachment panel(s), graphic(s), color element(s), wetness indicator(s), and so forth, as well as combinations comprising at least one of the foregoing designs. Optionally, e.g., to assist consumers in evaluation of a product, the package visual elements can have a size that is greater than or equal to about 90% of the article visual elements size, or, more specifically, a package visual elements size that is greater than or equal to about 95% of the article visual elements size, or, even more specifically, a package visual elements size that is substantially equal to about the article visual elements size.

The packaged article can comprise a combination of poly-film and visual element outer packaging where the visual element included a simulant of the article outer cover as well as the article refastening closure system, and the graphics (design and color) of the article. The outer package can act as a protective barrier for transit. The articles can be contained within the outer packaging in internal packages (e.g., about 5 to about 15 articles), wherein the internal packages can have an outer surface that is also a simulant of the articles and/or that has an aesthetic configuration (e.g., that has color(s) and/or design(s) that are compatible with the aesthetics of an area where the internal package(s) will be displayed (e.g., a child's room, a family room, a living room, a bath room, and so forth).

The packaging material can be a single or multi-layer plastic material having the desired look and texture(s), and having sufficient structural integrity to retain the enclosed product (e.g., absorbent article). The packaging material can have a basis weight of less than or equal to about 3.0 ounces per square yard (osy) or, more specifically, less than or equal to about 2.0, or, even more specifically, less than or equal to about 1.5 osy. For example, the packaging material can comprise: a nonwoven material (e.g., a structure of individual fibers or threads that are interlaid in an irregular, non-identifiable manner), tricot, rib knit, raschel knit, jersey knit, flannel, interlock knit, pique knit, pointelle knit, felted nonwoven, brushed twill, brushed satin, sateen, outing flannel, flannelette, fleece, and so forth, as well as combinations comprising at least one of the foregoing materials.

Nonwoven materials can be formed using many processes such as, for example, meltblowing processes, spunbonding processes, air laying processes, bonded carded web processes, and so forth, as well as combinations comprising at least one of the foregoing processes. Various layers of the packaging material can comprise nonwoven materials formed in different fashions. The basic weight of nonwoven materials may be expressed in ounces of material per square yard (osy) or grams per square meter (gsm), and the fiber diameters useful may be expressed in micrometers (Note that to convert from osy to gsm, multiply osy by 33.91).

The nonwoven material can comprise a meltblown material (e.g., web, fabric, and so forth). Meltblown fibers can be formed by extruding a molten thermoplastic material through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. A meltblown process is disclosed, for example, in U.S. Pat. No. 3,849,241 to Butin, et al. Generally speaking, meltblown fibers may be microfibers that may be continuous or discontinuous, are generally less than or equal to about 10 micrometers in diameter, and are generally tacky when deposited onto a collecting surface.

Alternatively, or in addition, the nonwoven material can comprise a spunbond material. Spunbonded fibers are small diameter substantially continuous fibers that are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. Spunbond fibers are generally not tacky when they are deposited onto a collecting surface. The production of spun-bonded nonwoven webs is described and illustrated, for example, in U.S. Pat. No. 4,340,563 to Appel, et al. U.S. Pat. No. 3,692,618 to Dorschner, et al., U.S. Pat. No. 3,802,817 to Matsuki et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al. Spunbond fibers can sometimes have diameters less than or equal to about 40 micrometers, and are often about 5 micrometers to about 20 micrometers in diameter.

For example, the nonwoven material can comprise a spunbond/meltblown/spunbond ("SMS") structure. The SMS structure comprises a meltblown layer (e.g., web, fabric, and so forth) sandwiched between two spunbond layers (e.g., web, fabric, and so forth). Possible SMS structures (e.g., laminates) are commercially available from Kimberly-Clark Corporation under marks such as Spunguard® and Evolution®. Some SMS materials are also described in U.S. Pat. Nos. 4,041,203 and 4,766,029 to Brock et al.; U.S. Pat. No. 5,464,688 to Timmons et al.; and U.S. Pat. No. 5,169,706 to Collier et al. The spunbonded layers on the SMS laminates can provide durability while the internal meltblown layer can provide porosity and additional cloth-like feel.

Suitable nonwoven materials can optionally comprise bonded carded webs and/or airlaid webs. Bonded carded webs can be formed from staple fibers sent through a combing or carding unit, which separates or breaks apart and aligns the staple fibers to form a nonwoven web. Once the web is formed, it can then be bonded. In the airlaying process, bundles of small fibers having typical lengths of about 6 millimeters (mm) to about 19 millimeters can be separated and entrained in an air supply and then deposited onto a forming screen, usually with the assistance of a vacuum supply. The randomly deposited fibers can then be bonded to one another using various bonding techniques.

Suitable plastic materials for making the nonwoven materials include thermoplastic materials such as polyolefins, polyesters, polyamides, polycarbonates, polyurethanes, polyvinylchloride, polytetrafluoroethylene, polystyrene, polyethylene terephthalate, biodegradable polymers (such as polylactic acid), and so forth, as well as copolymers and combinations comprising at least one of the foregoing thermoplastics. Possible polyolefins include, but are not limited to, polyethylene (e.g., high density polyethylene, medium density polyethylene, low density polyethylene, or linear low density polyethylene); polypropylene (e.g., isotactic polypropylene, syndiotactic polypropylene, atactic polypropylene); polybutylene (e.g., poly(1-butene) or poly(2-butene)); polypentene, (e.g., poly(1-pentene) or poly(2-pentene)); poly(3-methyl-1-pentene); poly(4-methyl 1-pentene); and so forth, as well as copolymers and combinations comprising at least one of the foregoing thermoplastics. Some possible copolymers include random and block copolymers prepared from two or more different unsaturated olefin monomers, such as ethylene/propylene and ethylene/butylene copolymers. Suitable polyamides include nylon 6, nylon 6/6, nylon 4/6, nylon 11, nylon 12, nylon 6/10, nylon 6/12, nylon 12/12, and copolymers of caprolactam and alkylene oxide diamine. Suitable polyesters include polyethylene terephthalate, polytrimethylene terephthalate, polybutylene terephthalate, polytetramethylene terephthalate, polycyclohexylene-1,4-di-methylene terephthalate, and isophthalate copolymers thereof. Optionally, the thermoplastic material can comprise a combination comprising at least one of any of the foregoing thermoplastic materials. For example, the packaging material can comprise a polyolefin with a low melting point (less than or equal to about 120 degree centigrade (° C.), or, more specifically, less than or equal to about 110° C., or, even more specifically, less than or equal to about 100° C.). Such a low melting polyolefin provides the advantage of ease of sealability of the packaging material, enhances the use of this packaging material for applications involving stack/overlap sealing. In addition, the use of a polyolefin with a low melting point, in combination with an inner layer comprising a polyester, provides the article of manufacture made therefrom with high seal strength.

Optionally, the packaging material may be reinforced. Possible reinforcement includes materials that provide structural integrity while not adversely affecting the desired aesthetics and texture(s) of at least the outer surface of the packaging material. Some possible reinforcements include scrim, gauze, netting, yarn, and so forth, as well as combinations comprising at least one of the foregoing reinforcements. A scrim comprises an open mesh of continuous filaments or yarns running both in the machine direction (length) and the cross machine direction (width) of the web. The filaments or yarns can comprise any suitable material that is compatible with the nonwoven material. The continuous filaments of the scrim material can impart the requisite tensile strength to the packaging material both in the machine direction and the cross machine direction. The scrim can be formed from various thermoplastic materials such as those listed above. For example, the scrim can comprise polyolefin (such as polyethylene or polypropylene), poly(butylene terephthalate), polyethylene terephthalate, Nylon 6, Nylon 6/6, and so forth, as well as combinations comprising at least one of the foregoing.

Optionally, for protection of the product (e.g., absorbent articles) within the packaging, liquid impermeable, film layer(s) can also be employed. In order to attain the desired aesthetics and texture(s), the film layer can be disposed internal to the outer surface of the packaging. One possible type of film that may be used is a nonporous, continuous film. Possible film materials include various plastic materials such as poly(vinyl alcohol), polyvinyl acetate, ethylene vinyl alcohol, polyurethane, ethylene methyl acrylate, ethylene methyl acrylic acid, and so forth, as well as combinations comprising at least one of the foregoing materials. If desired, the film may further comprise fillers, for example, calcium carbonate, titanium dioxide, or so forth, e.g., to increase opacity, decrease cost, or the like.

The packaging can be formed by bonding, stitching, and/or sealing the packaging material, e.g., to form a bag. The bonding or sealing can be accomplished with an adhesive, bonding material, by heating (e.g., fusing portions of the packaging material to other portions of the packaging material; such as thermal sealing, melt-bead sealing, impulse sealing, dielectric sealing, ultrasonic sealing), heat and pressure, pressure, and so forth, as well as combinations comprising at least one of the foregoing processes. For example, a heat seal can be formed by heating regions of the packaging material to at least their respective seal initiation temperatures, and applying pressure. The heating can be performed in a wide variety of manners, such as using a heated bar, hot wire, hot air, infrared radiation, ultrasonic sealing, and so forth, as well as combinations comprising at least one of the foregoing heating methods. Exemplary seals include end-seal(s), side-seal(s), L-seal(s) (i.e., sealed across the bottom and along one side, with an open top), a pouch (i.e., sealed on three sides, with an open top), and so forth.

The design (e.g., geometry, features, aesthetics (e.g., pictures and so forth) of the package is not limited. For example, the packaging can have zones of weakness (e.g., defined by perforations) to facilitate opening of the packaging, removal of the product from the packaging, and/or facilitate access to various levels of product. The package can have handle(s) for ease of carrying. Artistic design(s) can be disposed on the outer surface of the package for various purposes, brand identification, product identification (e.g., a design similar to the design of the product in the bag), and so forth.

The product within the package, for example, can be absorbent articles. The articles can be in a single or multiple layers. Disposable absorbent articles find widespread use as personal care products such as diapers, children's toilet training pants and other infant and child care products, adult incontinence garments and other adult care products, sanitary napkins and other feminine care products, bandages (e.g., surgical bandages, consumer bandages (e.g., Band-Aid® (or the like), and sponges . . . ), and so forth. In one embodiment, the absorbent article (e.g., a diaper, training pant, and so forth) can comprise a liquid permeable bodyside liner, an outer cover, and an absorbent body disposed between the bodyside liner and the outer cover. The packaging can be designed to simulate the texture(s) and/or aesthetics of the article; e.g., to have a similar look and feel as the outer cover. For example, the packaging can simulate the outer cover of Huggies® Brand Diapers, Huggies® Little Swimmers™, Goodnites®, Pull-Ups®, and so forth.

EXAMPLE

Various tests were performed to determine the differences in tactile feel and thermal feel between poly-film (namely 0.002 inches thick low density polyethylene (LDPE) film), and SMS (namely 1.5 osy LDPE spunbond/meltblown/spunbond; each layer being 0.5 osy). The tactile feel was determined using surface and bending tests. With respect to the surface properties, there were two test modes: (i) a simultaneous friction and roughness measurement, and (ii) a friction only measurement. In the simultaneous mode, the probe is a single steel wire with a diameter of 0.5 millimeters (mm), while in the friction only mode, the probe uses 10 single wires. A contact force of 10 grams (g) was used for the single wire probe, while 50 g is used for the multi-wire probe. The test speed was set at 1 millimeter per second (mm/s) for both test modes. The values measured included: (1) frictional measurements of mean value of the coefficient of friction (MIU), and the mean derivation of MIU (MMD), both of which are dimensionless; and (2) a roughness measurement of the mean deviation of surface thickness in micrometers (µm) (SMD). The measurements were taken in the machine direction (MD) and the cross direction (CD).

The average (Avg) test results (using 5 samples for each average) are set forth in Table 1 along with the standard deviation (Stdev). Sample 1 represents poly-film without any printing, Sample 2 represents poly-film with printing, Sample 3 represents SMS without any printing, and Sample 4 represents SMS with printing.

TABLE 1

| Sample No. | MD MIU | MD MMD | MD SMD (µm) | CD MIU | CD MMD | CD SMD (µm) | Mean MIU | Mean MMD | Mean SMD (µm) |
|---|---|---|---|---|---|---|---|---|---|
| 1: Avg | 0.131 | 0.0074 | 0.41 | 0.128 | 0.0074 | 0.29 | 0.130 | 0.0074 | 0.35 |
| Stdev | 0.004 | 0.0029 | 0.44 | 0.012 | 0.0004 | 0.04 | 0.006 | 0.0017 | 0.23 |
| 2: Avg | 0.127 | 0.0082 | 0.17 | 0.134 | 0.0089 | 0.21 | 0.131 | 0.0086 | 0.19 |
| Stdev | 0.004 | 0.0007 | 0.03 | 0.010 | 0.0007 | 0.05 | 0.003 | 0.0006 | 0.03 |
| 3: Avg | 0.525 | 0.0332 | 3.46 | 0.503 | 0.0395 | 4.75 | 0.514 | 0.0364 | 4.11 |
| Stdev | 0.023 | 0.0037 | 0.31 | 0.049 | 0.0024 | 0.27 | 0.027 | 0.0015 | 0.19 |
| 4 Avg | 0.424 | 0.0524 | 3.85 | 0.395 | 0.0646 | 5.22 | 0.410 | 0.0585 | 4.54 |
| Stdev | 0.060 | 0.0075 | 0.26 | 0.018 | 0.0020 | 0.55 | 0.029 | 0.0039 | 0.25 |

As can be seen from the data above, SMS materials show significantly higher friction values (MIU) compared to less textured poly-film materials. The mean SMS values were greater than or equal to about 0.30, or more specifically, greater than or equal to about 0.35, or, even more specifically, greater than or equal to about 0.40, and even greater than or equal to about 0.50. The poly-film materials had mean MIU values consistently less than 0.15. In other words, the SMS material had substantially more texture than the poly-film materials. With respect to MMD, the poly-film had mean MMD values consistently less than 0.0100. The SMS had mean MMD values of greater than or equal to about 0.0200, or more specifically, greater than or equal to about 0.0300, or, even more specifically, greater than or equal to about 0.0350, and even greater than or equal to about 0.0550. A substantial difference in surface thickness was also noted. The poly-film had mean SMD values of less than 0.50 µm. The SMS material had mean SMD values of greater than or equal to about 2.0 µm, or more specifically, greater than or equal to about 2.5 µm, or, even more specifically, greater than or equal to about 3.0 µm, and even greater than or equal to about 4.0 µm.

The materials (Samples 1-4) were also tested for bending results. It was discovered that the SMS material was substantially stiffer than the poly-film material, yet was also much quieter when handled. This stiffness can make the material seem more substantial, giving it more appeal to the consumer; an appearance of higher quality. The poly-film, Sample 1, had a mean bending stiffness grams force—square centimeters per centimeter (gf·cm²/cm) average of 0.078 with a standard deviation of 0.002 gf·cm²/cm.

Finally, the materials (Samples 1-4) were also tested for thermal properties, e.g., to determine the cool/warm feel by measuring the maximum heat flux flows to the sample when a pre-heated copper plate (10° C. higher than the ambient temperature; with a size of 3 centimeter (cm) by 3 cm) comes into physical contact with the sample surface that was conditioned in a TAPPI (Technical Association of the Pulp and Paper Industry) condition. Higher $Q_{max}$ values indicate cooler feel while lower $Q_{max}$ values indicate warmer feel, while $Q_{max}$ is given in watts per square meter (W/m²). The average test results (using 3 samples for each average) are set forth in Table 2.

TABLE 2

| Sample No. | $Q_{max}$ (W/m²) |
|---|---|
| 1: Avg | 0.165 |
| Stdev | 0.004 |
| 2: Avg | 0.126 |
| Stdev | 0.002 |
| 3: Avg | 0.090 |
| Stdev | 0.002 |
| 4: Avg | 0.084 |
| Stdev | 0.002 |

Since the SMS materials have a significantly lower $Q_{max}$, they have a warmer feel. In some embodiments, the packaging material can have a $Q_{max}$ of less than or equal to about 0.100 W/m², or, more specifically, less than or equal to about 0.095 W/m², or, more specifically, less than or equal to about 0.090 W/m². As can be seen from Table 2, poly-film material has a $Q_{max}$ of greater than 0.160 W/m² without print (Sample 1), and greater than 0.125 W/m with print (Sample 2). The SMS material had a $Q_{max}$ of less than 0.0.93 W/m² without print (Sample 3), and less than 0.085 W/m² with print (Sample 4). The SMS Sample 3 had a 45% lower $Q_{max}$ than Sample 1, poly-film, while SMS Sample 4 had a 33% lower $Q_{max}$ than Sample 2, poly-film.

Optionally, due to the texture(s) and appearance of the packaging material the consumer can have an idea of the texture(s) and appearance of the absorbent article inside the package; e.g., an essence of the quality and/or desirability of the product. For example, a diaper outer cover can have a cloth-like softness and so can the packaging outer surface. Moreover, the appearance of the package can distinguish it from poly-film packages, providing a marketing, sales, and shelf advantage. The packaging can actually illustrate the quality of the product within the packaging. Finally, since the noise related to the opening of the package and/or removal of product can be reduced as compared to poly-film packaging, the (single or multi) textured packaging has enhanced desirability since product can be discreetly removed; e.g., it is less likely to cause a disturbance when opened and/or when product is removed (e.g., may not awaken a sleeping/groggy baby).

In another embodiment, the cloth-like packaging can be disposed around small groupings of the absorbent article (e.g., about 5 to about 40 articles, or, more specifically, about 5 to about 30 articles, or, even more specifically, about 5 to about 25 articles, and, yet even more specifically, about 5 to about 10 articles), and the small groupings can be disposed in an outer packaging or cover, e.g., cloth-like and/or poly-film (wherein the covering can be partially or wholly transparent). The small group packaging can have various aesthetic features such that, upon disposal of the outermost packaging, the small grouping can be disposed throughout a home, for example, and discretely contain the desired absorbent product in a displayable packaging. Such packaging can portray a higher quality and artistic benefit, can simplify organization of articles, and can maintain the articles in a clean environment prior to use (e.g., dispensed in the small group packaging rather than removed from all packaging prior to use).

Optionally, the packaging can include a closing and fastening system (e.g., a refastenable closure system), e.g., to maintain the cleanliness of the articles. In order to further enhance the portrayal of product information to a customer, to further distinguish the products within the packaging (e.g., from competitor products (e.g., other diapers, feminine products, and so forth)), to further appeal to the customer, and/or to gain the "wow" factor (i.e., for enhanced marketability), the package refastening system can optionally be the same or similar to (e.g., a simulant) of the product refastening closure system (e.g., the diaper closures). Exemplary fastening systems include hook and loop fastener(s) (e.g., Velcro®), tape, tab fastener(s), mushroom and loop fastener(s), cohesive(s), adhesive(s) snap(s), button(s), pin(s), microfiber foam, and so forth, as well as combinations comprising at least one of the foregoing fasteners. These fastening systems can be employed with the overall packaging and/or for the packaging enclosing the small groupings of articles (e.g., about 5 to about 25 articles).

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A package containing an article, wherein the article comprises a first article texture and a second article texture, the package comprising:
   a plastic packaging material having an outer surface;
      wherein the outer surface comprises a nonwoven material;
      wherein the first article texture and the second article texture are non-similar, at least a portion of the outer surface has a first packaging texture that is a simulant of the first article texture and at least a portion of the outer surface has a second packaging texture that is a simulant of the second article texture; and
      wherein the article is a diaper, a training pant, an adult-incontinence garment, or disposable underwear.

2. The package of claim 1, wherein the article comprises an outer cover and a fastening element attached to the outer cover, the outer cover comprises the first article texture and the fastening element comprises the second article texture.

3. The package of claim 1, wherein the outer surface comprises two or more nonwoven materials.

4. The package of claim 1, wherein the nonwoven material comprises a spunbond material.

5. The package of claim 1, wherein the plastic packaging material is a multi-layer material comprising a spunbond-meltblown-spunbond construction.

6. The package of claim 1, wherein the nonwoven material comprises polyethylene.

7. The package of claim 1, wherein the plastic packaging material further comprises a film layer disposed between the nonwoven material and the article.

8. The package of claim 1, wherein the plastic packaging material comprises reinforcement selected from the group consisting of scrim, gauze, netting, knit, yarn, and combinations comprising at least one of the foregoing reinforcements.

9. The package of claim 1, wherein the article comprises disposable absorbent articles.

10. The package of claim 9, wherein the article comprises a liquid permeable bodyside liner, an outer cover, and an absorbent body located between the bodyside liner and the outer cover, and wherein the outer cover comprises the first article texture.

11. The package of claim 10, wherein the packaging material has a $Q_{max}$ of less than or equal to about 0.100 W/m$^2$.

12. The package of claim 1, wherein the packaging material has a MIU of greater than or equal to about 0.30.

13. The package of claim 1, wherein the packaging material has a MMD of greater than or equal to about 0.0200.

14. The package of claim 1, wherein the packaging material has a mean SMD value of greater than or equal to about 2.0 μm.

15. The package of claim 1, further comprising a package refastenable closure system.

16. The package of claim 15, wherein the refastenable closure system is a simulant of an article refastenable closure system.

17. The package of claim 16, wherein the package refastenable closure system is selected from the group consisting of hook and loop fastener, tape, tab fastener, mushroom and loop fastener, cohesive, adhesive, snap, button, pin, microfiber foam, and combinations comprising at least one of the foregoing fasteners.

18. The package of claim 17, wherein the package refastenable closure system is selected from the group consisting of hook and loop fastener, tape, tab fastener, mushroom and loop fastener, cohesive, adhesive, and combinations comprising at least one of the foregoing fasteners.

* * * * *